United States Patent [19]

Keggins et al.

[11] Patent Number: 4,544,637

[45] Date of Patent: Oct. 1, 1985

[54] CULTURE MEDIA FROM CLARIFIED DIARY WHEY LACTOSE PERMEATES

[75] Inventors: Kathleen M. Keggins, Glen Burnie; Ann C. Davis, College Park; Edward M. Sybert, Ellicott City; Thomas D. Mays, Burtonsville; Robert A. Milch, Baltimore, all of Md.

[73] Assignee: IGI Biotechnology, Inc., Columbia, Md.

[21] Appl. No.: 418,067

[22] Filed: Sep. 14, 1982

[51] Int. Cl.[4] .......................... C12N 1/20; C12N 1/00
[52] U.S. Cl. ..................................... 435/253; 435/243
[58] Field of Search ..................... 426/34, 41, 61, 583; 435/243, 253, 255, 260

[56] References Cited

U.S. PATENT DOCUMENTS

| | | | |
|---|---|---|---|
| 2,123,203 | 1/1936 | Riggs et al. | 426/583 |
| 3,922,375 | 11/1975 | Dalan et al. | 426/583 |
| 3,930,039 | 12/1975 | Kuipers | 426/41 |
| 4,036,999 | 7/1977 | Grindstaff | 426/41 |
| 4,143,174 | 3/1979 | Shah et al. | 426/583 |
| 4,202,909 | 5/1980 | Pederson | 426/583 |
| 4,402,986 | 9/1983 | Sinkoff et al. | 435/253 |

OTHER PUBLICATIONS

Stieber et al., Prod. of Lactobacillus Cells by Dialysis Continuous Fermentation of Deproteinized Whey, 1980, J. Dairy Sci. 63:722–730.

Primary Examiner—Raymond N. Jones
Assistant Examiner—Marianne S. Minnick
Attorney, Agent, or Firm—Haight & Associates

[57] ABSTRACT

A method for separating bacteriological growth inhibitors from sweet whey ultrafiltrate to form a mother liquor which is useful as a bacteriological culture media and a precipitate which is useful as a food grade additive to cause clouding, stabilization, emulsification, and thickening of food, pharmaceutical, and cosmetic compositions.

17 Claims, No Drawings

CULTURE MEDIA FROM CLARIFIED DIARY WHEY LACTOSE PERMEATES

DESCRIPTION OF THE INVENTION

1. Technical Field of the Invention

This invention relates to processes for converting sweet dairy whey ultrafiltrates into commercially useful end products. More particularly, this invention relates to a process for treating protein-free sweet dairy whey permeate with a Lewis base to form a precipitate which can be converted to a dry, free-flowing, odorless and tasteless product useful in the food, pharmaceutical, and cosmetics industries. The mother liquor which is separated from the precipitate can be converted into a wide variety of bacteriological culture media useful in industrial and clinical microbiology.

2. Background Art

As noted by Alan G. Lane in J. Appl. Chem. Biotechnol. 27: 165-169 (1977), the disposal of whey resulting from the manufacture of cheese and casein presents problems of enormous magnitude, with the annual production of whey in the United States estimated to have a pollution strength equivalent to the sewage from 10 million people. While some whey is used as a livestock feed (e.g. see U.S. Pat. Nos. 3,343,962 and 3,497,359 to Herbert R. Peer), most has been regarded as waste and disposed of by traditional methods. While recent developments in ultrafiltration (UF) technology have made it possible to economically recover proteins from whey, disposal of the remaining protein-free ultrafiltrate presents serious difficulties since it contains most of the lactose (about 45 g/l) and thus most of the pollutional strength from the original whey.

In one approach to this problem, fermentation techniques have been developed for converting the lactose into food yeasts, e.g. *Kluyveromyces fragilis,* thereby attempting to overcome the limited market for lactose itself. Such processes have generally involved fermentation of the whey or the whey ultrafiltrate, first without prior concentration and later by dialysis culture techniques such as reported by Lane. While offering the potential for removing up to 90 percent of the lactose present in the whey ultrafiltrate, such methods suffer the disadvantage of yielding a single product of limited utility.

The dialysis continuous fermentation of deproteinized whey has been applied to the production of Lactobacillus cells, e.g. as reported by R. W. Steiber et al. in J. Dairy Sci. 63: 722-730 (1980). Using deproteinized whey as the substrate, the fermentor contents are maintained at a constant pH of 5.5 by the addition of ammonia and dialyzed through a semipermeable membrane against water; cell production was double that of ordinary continuous fermentation.

Both sweet whey permeate and acid whey permeate have been used as a feedstock in ethanol production using $\beta$-galactosidase and *Saccharomyces cerevisiae,* e.g. as reported by Barbel Hahn-Hagerdal in Applied Biochemistry and Biotechnology 7: 43—45 (1982). Although more than 50 percent of the lactose was converted to ethanol, the eluate contains less than 2 percent ethanol yield based on the weight/unit volume of whey permeate feedstock.

Whey permeates have also found use in cheese starter cultures. For example, G. H. Richardson described in Dairy and Ice Cream Field (September, 1978) the use of whey permeate in producing bulk cultures or starters for cheese production as an alternative to the use of expensive phage inhibitory media. This process, The Utah State University Lactic Culture System, is further described by Lynn L. Jonas et al. in Cultured Dairy Products Journal: 12-14 (May 1977), in Utah Agricultural Experiment Station Report 42 (August 1979), and in Canadian Pat. No. 1,024,393. Briefly, fresh liquid whey is added to the bulk tank and diluted to approximately 3-4 percent lactose with tap water. Stimulants, essential nitrogen sources, and phosphates are added to the solution, and ammonia gas is added during incubation to maintain the pH at about 6.2. The bulk tank contents are heated to 90° C. for 45 minutes to kill phage and cooled to 27° C. for inoculation; the resultant concentrates are reported to have been stable for at least three weeks.

The use of whole whey as a bacteriological culture medium has been reported by Emel Celikkol in Mikrobiyol. Bul. 9(4): 273-279 (1975) and in U.S.S.R. Pat. No. 819,166. As summarized in Chem. Abs. 84: 72629u and 95: 59904n respectively, the former process uses untreated whole whey, while the latter process removes lactose from the initial whey and hydrolyzes the proteins therein; neither of these methods has gained widespread use.

Acid whey colloidal precipitates have found use as clouding, stabilizing, emulsifying, thickening, and gelling additives (depending in general on the concentration in which the precipitate is employed) to food grade compositions, e.g. as described by U.S. Pat. Nos. 4,143,174 and 4,209,503 to Syed M. M. Shah et al., the contents of which are incorporated by reference herein. Because they can be dried to a free-flowing powder and exhibit no disagreeable taste, such materials are useful as food additives, pharmaceutical carriers, cosmetic bases, dentifrice bases, etc. However, their property of gelling water and petroleum ether is undesirable for certain applications.

DISCLOSURE OF THE INVENTION

Accordingly, it is a general object of the present invention to provide a method for converting deproteinized sweet whey permeates into industrially useful products.

Another object of the present invention is to provide an improved general purpose bacteriological culture medium.

A further object of the present invention is to provide improved special purpose bacteriological culture media.

An additional object of the present invention is to provide improved pre-reduced anaerobic bacteriological culture media.

A more particular object of the present invention is to provide improved food grade additives for use in foods, pharmaceutical carriers, cosmetic bases, dentifrice bases, and the like.

Upon study of the specification and appended claims, further objects, features and advantages of the present invention will become more fully apparent to those skilled in the art to which this invention pertains.

BEST MODE FOR CARRYING OUT THE INVENTION

Briefly, the above and other objects, features and advantages of the present invention are attained in one aspect thereof by providing a method for separating a microcrystalline solid phase from sweet whey ultrafiltrate to form a mother liquor which is useful as a bacteriological culture media and a precipitate which is useful as a food grade additive to cause clouding, stabilization, emulsification, and thickening of food, pharmaceutical, and cosmetic compositions.

In one aspect, the present invention provides a general purpose bacteriological culture medium prepared from an essentially protein-free ultrafiltration permeate of sweet whey which is useful both in industrial scale processes and as a starting material for the preparation of various bacteriological culture media which are useful in clinical diagnostic methods. Suitable deproteinized whey syrup solids (WSS) which can be used as starting materials are commercially available or can be prepared by techniques known to those skilled in the art.

The WSS starting material, either in spray dried form or obtained in a liquid stream at a concentration of 5–40 percent (wt/vol), is first diluted with water to a concentration of 2–20 percent, preferably about 3.5 percent solids. Concentrations much below this range yield a final product which has an inadequate nutrient content, while concentrations much above this range yield a finel product which fails to stay in solution and has excess nutrients which may inhibit certain microorganism growth. Excessively high concentrations also impedes the removal of WSS components which have been found either to inhibit or not sustain adequate growth of microorganisms of industrial or clinical interest.

These inhibitory components, present along with other components which are collectively referred to herein as the "cloud retenate", are removed as a microcrystalline solid phase from the diluted WSS by the addition of sufficient non-toxic Lewis base, preferably an inorganic base such as ammonium hydroxide or alkali metal hydroxide and especially ammonium hydroxide (which can be generated in situ by bubbling ammonia gas through the diluted WSS, forming the relatively nontoxic ammonium ion) to raise the pH of the diluted WSS to about 8–10, preferably to about pH 9. This increase in the pH of diluted WSS results in precipitation of the cloud retenate, with maximal yield obtained at about pH 9. The precipitate is physically separated from the mother liquor, e.g. by centrifugation at 12,000 g and 0.45μ filtration or preferably by ultrafiltration across a 20K to 100K (KiloDaltons) molecular weight exclusion membrane, and saved for use as a food grade additive as discussed below. Centrifugation alone without subsequent filtration is generally unsatisfactory, since the clear supernatant frequently turns cloudy upon subsequent autoclaving. Ultrafiltration across a smaller membrane, e.g. 10K, is unsatisfactory since the culture medium shows poor growth compared to one which has been filtered across a 20K or higher membrane.

The resultant mother liquor, from which the cloud retentate has been physically separated, can be used as a general purpose microbiological growth medium since it contains metabolically useful quantities of assimilable carbon, nitrogen, and phosphorous. The principal carbon source is the lactose present in WSS, together with roughly equivalent amounts of glucose and sucrose and a lesser amount of galactose. Typical available sugar contents in unsupplemented media after autoclaving are: 53.0 percent β-lactose (11.8 mg/ml); 44.8 percent sucrose+α-lactose (9.97 mg/ml); 1.2 percent galactose (0.27 mg/ml); and 1.0 percent glucose (0.23 mg/ml).

For use with microorganisms which do not normally metabolize lactose, or for use in clinical screening applications where such organisms may be encountered, the metabolizable carbon content can be enhanced by the addition of some glucose, generally to a total concentration of about 0.5 mg/ml.

It has been found that WSS, although they are essentially protein free, contain adequate amounts of metabolizable nitrogen in the form of free amino acids and low molecular weight polypeptides. Thus, in accordance with the present invention, there is no need to hydrolyze separated proteins to increase the nitrogen content as described in U.S.S.R. Pat. No. 819,166; in any event, most proteins have already been removed during the ultrafiltration process and are not available as a component of the WSS starting material. If supplementation of nitrogen sources is desired, it can be achieved by the addition of conventional nitrogen sources, e.g. peptone, casamino acids, yeast extracts, etc. In many cases nitrogen supplementation will not be required, even though the medium's Lowry protein content is only a fraction of that in two widely used clinical culture media as shown in Table 1; a typical amino acid analysis is shown in Table 2:

TABLE 1

LOWRY PROTEIN ANALYSIS

| Sample | mg/ml Protein |
|---|---|
| BBL Nutrient Broth | 4.8 |
| Difco Penassay Broth | 3.8 |
| WSS Medium | 1.2 |
| Skim Milk | 30.0 |

TABLE 2

AMINO ACID ANALYSIS

| Amino Acid | Approximate μ moles/ml × 10 |
|---|---|
| alanine | 38.9 |
| arginine | 10.5 |
| aspartic acid | 26.3 |
| glutamic acid | 94.5 |
| glycine | 19.1 |
| histidine | 9.3 |
| isoleucine | 18.8 |
| leucine | 33.8 |
| lysine | 30.9 |
| methionine | 10.8 |
| phenylalanine | 14.6 |
| serine | 45.6 |
| threonine | 19.0 |
| valine | 34.5 |

The basic medium exhibits good buffering capacity to both acid and base addition, as shown in Tables 3 and 4:

TABLE 3

ACID BUFFERING CAPACITY
pH after successive 0.1 ml additions
of 1N HCl to 25 ml broth

| | 0 | 1 | 2 | 3 | 4 | 5 |
|---|---|---|---|---|---|---|
| Penassay Broth | 6.92 | 6.64 | 6.34 | 5.96 | 5.28 | 4.37 |
| WSS Medium | 6.82 | 5.59 | 4.66 | 4.14 | 3.73 | 3.32 |
| Nutrient Broth | 6.80 | 4.38 | 3.58 | 3.04 | 2.60 | 2.31 |

TABLE 4

BASE BUFFERING CAPACITY
pH after successive 0.1 ml additions
of 1N NaOH to 25 ml broth

|  | 0 | 1 | 2 | 3 | 4 | 5 |
|---|---|---|---|---|---|---|
| Penassay Broth | 6.93 | 6.93 | 6.96 | 6.99 | 7.02 | 7.05 |
| WSS Medium | 6.80 | 6.93 | 7.04 | 7.17 | 7.31 | 7.45 |
| Nutrient Broth | 6.74 | 6.99 | 7.19 | 7.37 | 7.55 | 7.71 |

The basic medium can be used either in liquid form or spray-dried, preferably to a moisture content of less than 10 percent by weight, e.g. about 6 percent by weight, for greater storage stability. When preparing a liquid broth, any desired supplements can be added prior to autoclaving at 121° C. for 15–20 minutes. In this manner, various types of culture media can be readily prepared from the basic medium. Presently preferred media are: (1) a general purpose growth medium supplemented with about 0.5 percent casamino acids and 0.05 percent yeast extract (and 0.05 percent glucose for use with non-lactose fermenting enteric microorganisms) which compares favorably to widely used general nutrient broths, e.g. Difco Penassay broth, Oxoid Lablemco broth and Nutrient Broth α2, and BBL nutrient broth; (2) a medium for the cultivation of both aerobic and anaerobic bacteria from primary clinical specimens supplemented with 0.5 percent casamino acids, 0.5 percent yeast extract, about 0.1 percent agar or other gelling agent to reduce oxygen diffusion, 0.5 percent cysteine HCl as a reducing agent and having a total glucose content of about 0.4 percent which when boiled before use to reduce the oxygen content compares favorably to widely used thioglycollate broth; and (3) a pre-reduced, sterile, anaerobically prepared medium for the cultivation of facultative and obligate anaerobic bacteria which is supplemented with 0.5 percent casamino acids, 1 percent yeast extract, total 0.5 percent glucose, and 0.001 percent resazurin as an oxidation-reduction indicator. The latter medium is boiled under a nitrogen atmosphere for approximately 10 minutes and then supplemented with 0.2 percent cysteine HCl, 0.50 mg/ml hemin, 1 mg/ml vitamin K$_3$, and adjusted to pH 7.8 with ammonium hydroxide prior to being stored under a nitrogen atmosphere. This medium has an oxidation-reduction potential of −150 mV or lower, and the colorimetric redox indicator turns pink upon oxidation of the medium.

While relatively unimportant for use in industrial fermentation processes, the optical clarity of a broth culture medium is highly important in clinical applications. For this purpose, it is advisable to screen samples of supplements intended to be used, as in some instances it has been found that certain samples will not yield the desired clear product. At high yeast extract concentrations of around 1 percent, Amberex 510 water soluble autolyzed yeast extract obtained from Amber Labs, Juneau, Wis. and Nestle yeast extracts obtained from Baltimore Biological Laborartory have proved satisfactory. Amino acid supplements from Difco Laboratories and U.S. Biochemical are likewise satisfactory for use in the present process.

Liquid culture media can be sterilized by conventional techniques such as sterile filtration or autoclaving. Once autoclaved, it should not be re-autoclaved, as this causes a material reduction in microbial growth. If sterile filtration alone is employed, generally through a 0.22$\mu$ filter, it is necessary to reduce the pH of the broth to about 6.8–7.1 by the addition of a suitable nontoxic acid such as HCl. This can be accomplished either before or after filtration, but in any event must be done prior to most culture applications. Since ultrafiltration, e.g. through a 20K cutoff membrane, may also remove residual emulsified fats and other inhibitory materials, it can advantageously be used prior to autoclaving. Sterilization of liquid culture media by autoclaving has been found to inherently reduce the pH thereof from about pH 9 to the desired range, and for that reason an initial pH adjustment to pH 9 together with autoclaving is presently preferred. The reason for this is not fully known, but may be the result of polypeptides or other organic buffering constituents of the medium being degraded by the heat of autoclaving.

In addition to its use as a broth, the basic and supplemented culture media of the present invention can be made up into solid or semisolid plates or slant tubes by the addition of a gelling agent such as agar agar, Carrageenan, pectin, silicone gel, guar gum, locust bean gum, various gellable polysaccharides, etc. according to known techniques. These gelling agents can be used with or without other additives such as defibrinated sheep or horse blood, proteins, litmus, etc. to form culture media suitable for use as protease assay agar, blood agar, litmus agar, etc. For example, the liquid medium is easily prepared in the form of pour plates by the addition of 1.5 percent (wt/vol) agar. In general, the basic culture medium of the present invention can be modified as desired by the addition of a wide variety of supplements depending on its ultimate intended use, e.g. see the Media section at pages 601–656 of the American Type Culture Collection Catalogue of Strains I, 15th Edition (1982), the contents of which are incorporated by reference herein.

Alternatively, the culture media can be spray dried to a powder in order to increase shelf life and save transportation costs. Because the medium must be in a concentrated form for spray drying, the use of WSS starting materials in concentrations greater than the 3.5 percent generally employed for liquid media is preferred, and concentrations as high as 20 percent have proven satisfactory. As the solids content of the WSS starting material approaches 30 percent, it has been found that some of the solid material remains in suspension and is not precipitated out by pH adjustment. Spray drying of the basic medium containing supplements such as 0.05 percent yeast extract and 0.5 percent casamino acids is readily accomplished. Spray drying of unsupplemented basic medium generally requires drier air to compensate for the lack of seed particles in the supplements, which dry rapidly and form a nucleus upon which the rest of the materials can dry. Use of a portable, general-purpose spray drier such as that manufactured by Nitro Atomizer, Inc. of Columbia, MD is quite satisfactory with a temperature of about 200° C. and an outlet stack temperature of about 80° C. Using such conditions, the moisture content in the basic supplemented medium is reduced to about 6 percent.

It will be appreciated that the culture media of the present invention can also be employed as a starter ingredient, e.g. in the biological production of cheeses such as American, Swiss, Italian, cheddar, and cottage cheeses, and in the fermentation of beer, wine, sausages, silage, and antibiotics. Because the WSS starting material is initially derived from the manufacture of cheeses, these represent the currently preferred bulk starters. The use of whole whey-based cheese starter cultures is well known in the art as illustrated, inter alia, by G. W. Reinbold et al. U.S. Pat. No. 3,998,700; D. L. Andersen et al. U.S. Pat. No. 4,020,185; R. S. Porubcan et al. U.S. Pat. No. 4,115,199; and W. E. Sandine et al. U.S. Pat. No. 4,282,255. Because modestly high concentrations of phosphate or citrate buffers tend to inhibit the growth potential of the culture medium of the present invention, it is preferred that when used they be employed in a delayed-release form.

The cloud retentate which is precipitated at pH 9 and separated from the mother liquor by centrifugation or ultrafiltration across a 20K to 100K membrane is harvested as an aqueous pellet material which has the consistency of shortening at 4° C. and becomes more free-flowing upon warming to room temperature. When dried, this precipitate is a tasteless, odorless, chalky white free-flowing powder; typically, about 15 percent of the input WSS solid material processed is recovered as this dried precipitate powder. This material is different in nature from both unprocessed spray dried WSS and the precipitate that forms when spray-dried WSS are resuspended to 20 percent concentration (wt/vol) and cooled at 4° C. for 72 hours, as shown in Table 5. The data shown are from the same starting material sample, which had a maximum water solubility at room temperature of about 20 percent, a normal pH at that concentration of 5.5 to 6.0, and contained less than 1 mg/100 g. of carbohydrates and essentially no protein or fat. Data were obtained by IPC analysis according to Industrially Coupled Plasma-Atomic Emission Spectroscopy Method 3.005 of AOAC:

TABLE 5
ICP ANALYSIS OF CLOUD RETENTATE
mg/100 g Solids (Dry Basis)

|  | Freshly Resuspended Whey Syrup Solids (WSS) | 20 percent WSS 4° C., 72 hrs. Precipitate | 20 percent WSS pH 9 Precipitate |
|---|---|---|---|
| calcium | 348–438 | 53,920 | 15,800 |
| eron | .11–.12 | 66.5 | 6.59 |
| phosphorous | 488–491 | 7,828 | 11,448 |
| magnesium | 150 | 5,733 | 2,370 |
| zinc | .06–.08 | 7.59 | 3.42 |
| copper | .025 | 7.45 | .79 |
| sodium | 774–863 | 4,616 | 718 |
| chromium | .036–.037 | 4.80 | 1.57 |
| aluminum | 1.1–1.3 | 529.55 | 15.66 |
| barium | .025–.028 | 8.22 | .57 |
| strontium | .11–.22 | 15.35 | 6.60 |
| boron | .06–.07 | 36.95 | .631 |
| manganese | .005–.011 | 2.12 | .21 |

Unlike the superficially similar materials reported by Shah et al. in U.S. Pat. Nos. 4,143,174 and 4,209,503, the cloud retentate of the present invention is insoluble in both water and petroleum ether, as shown in Table 6.

TABLE 6
SOLUBILITY OF CLOUD RETENTATE

| Solvent | Solubility |
|---|---|
| Wet Pellet: | |
| ethyl acetate | insoluble |
| benzene | insoluble |
| toluene | insoluble |
| chloroform | insoluble |
| petroleum ether | insoluble |
| methanol | very cloudy suspension |
| ethanol | very cloudy suspension |
| propanol | very cloudy suspension |
| butanol | slight suspension |
| water | insoluble |
| 1N HCl | cloudy suspension |

TABLE 6-continued
SOLUBILITY OF CLOUD RETENTATE

| Solvent | Solubility |
|---|---|
| 1N NaOH | cloudy suspension |
| Resuspended Powder: | |
| water, 5 percent solids | insoluble |
| water, 10 percent solids | insoluble |
| water, 20 percent solids | insoluble |
| petroleum ether, 5 percent solids | slight suspension |
| petroleum ether, 10 percent solids | slight suspension |
| petroleum ether, 20 percent solids | slight suspension |

Taking into account these unique solubility properties, the hot air tray dried cloud retentate of the present invention can be employed as a food grade additive to pharmaceutical, cosmetic, and food materials using techniques known in the art, e.g. as described in the cited Shah patents.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

Preparation of Basic Culture Medium 7 g of WSS (commercially available from Express Foods Co.) was made up to 200 ml. with deionized water (3.5 percent solids content, wt/vol). The mixture was stirred for a few minutes to mix well, as some solids tend to fall out of solution if it the mixture is not stirred. The pH was increased from an initial pH of 6.09 to 8.99 by the addition of 2.15 ml of 5.5N $NH_4OH$ while stirring, and centrifuged for 10 minutes at 8500 rpm (11,800 g) in a Sorvall RC-5B centrifuge using a GSA rotor refrigerated at 4° C. 1.26 g of a soft, white cloud retentate pellet were obtained per 100 ml of starting material. The supernatant was poured through a 0.45$\mu$, 115 ml Nalgene filtration unit, yielding 200 ml of clear material having a pH of 9.04. After autoclaving at 15 psi for 20 minutes, a dull orange and crystal clear culture medium was obtained, having a final pH of 7.07.

As a control, the above process was repeated using whole whey as the starting material. The initial pH was 6.26, and 2.4 ml of $NH_4OH$ were added to bring the pH up to 8.98. Following centrifugation, 1.08 g of a hard, tan pellet were obtained per 100 ml of starting material. The supernate was not clear, but had fluffy material floating throughout it. Only about 25 ml of the supernate could be passed through the filter unit until it clogged and the filter had to be changed. Following filtration, the supernate was still cloudy and had a pH of 8.98. After autoclaving, a dull orange, cloudy liquid was obtained having a pH of 7.08.

EXAMPLE 2

Precipitation with Other Bases

The procedure of Example 1 was followed, but substituting KOH for the $NH_4OH$ used to adjust the pH. From an initial pH of 6.09, 0.2 ml of 6N KOH and 0.2 ml of 1N KOH were added to bring the pH to 8.92. 1.66 g of soft, white pellet were obtained per 100 ml of starting material. Following filtration, the supernate was clear and had a pH of 8.78. After autoclaving, the liquid was golden colored and very slightly cloudy, with a final pH of 6.25.

When NaOH was substituted for the NH₄OH of Example 1, the initial pH of 6.08 was raised to pH 8.90 by the addition of 0.45 ml of 3N NaOH. 1.62 g of soft, white pellet were obtained per 100 ml of starting material. Following filtration, the supernate was clear and had a pH of 8.75. After autoclaving, a golden colored, slightly cloudy liquid was obtained having a final pH of 6.25.

EXAMPLE 3

Comparative Growth Characteristics

Each of the culture media from Examples 1 and 2 were evaluated for their ability to support the growth of common laboratory culture strains, *Bacillus subtilis* 6051a, *Enterobacter aerogenes* E13048, and *Escherichia coli* HS. Tubes of culture broth, both unsupplemented and supplemented with 1 percent BBL yeast extract, 0.5 percent Difco casamino acids, and 0.5 percent sucrose (Sigma Chemical Co.) were inoculated and incubated at 35° C. for 5 hrs, after which optical density readings were made at 660 nm. Difco Penassay broth and BBL Nutrient broth were used as controls. The results in this and the following experiments were scored according to the following scale, which roughly correlates to half-log differences in measured optical density:

| | |
|---|---|
| ++++ | Excellent growth; O.D. 0.3–1.0 |
| +++ | Good growth; O.D. 0.1–0.3 |
| ++ | Moderate growth; O.D. 0.03–0.1 |
| + | Some growth; O.D. 0.005–0.03 |
| – | No growth; O.D. 0–0.005. |

The results are shown in Table 7.

TABLE 7

Preliminary Growth Screening

| Culture Medium | B. subtilis | Ent. aerogenes | E. coli |
|---|---|---|---|
| Difco Penassay broth | ++++ | ++++ | ++++ |
| BBL Nutrient broth | ++++ | ++++ | ++++ |
| 3.5 percent WSS (NaOH) | ++ | +++ | +++ |
| 3.5 percent WSS (NaOH) + supp | ++++ | ++++ | ++++ |
| 3.5 percent WSS (KOH) | ++ | +++ | +++ |
| 3.5 percent WSS (KOH) + supp | ++++ | ++++ | ++++ |
| 3.5 percent WSS (NH₄OH) | +++ | +++ | +++ |
| 3.5 percent WSS (NH₄OH) + supp | ++++ | ++++ | ++++ |

EXAMPLE 4

Evaluation of pH Importance

In order to evaluate the importance of the pH employed for precipitation of the cloud retentate, a series of culture media supplemented as in Example 3 were prepared in which the initial pH was adjusted to between 4 and 11 using HCl or NH₄OH as required. With the exception of the initial pH, the media were prepared as in Example 1 and the supplement added prior to autoclaving, at which time all of the samples appeared similar and filtered easily. The difference in the product obtained following autoclaving is shown in Table 8.

TABLE 8

| Process pH | Appearance After Autoclaving | Final pH |
|---|---|---|
| 4 with HCl | clear, light green | 4.5 |
| 5 with HCl | clear, light green | 5.5 |
| 6 no addition | slightly opaque | 6.0 |
| 7 with NH₄OH | very cloudy, light yellow | 6.5 |
| 8 with NH₄OH | very cloudy, golden | 6.5 |
| 9 with NH₄OH | clear, root beer color | 7.0 |
| 10 with NH₄OH | very dark brown | 8.5 |
| 11 with NH₄OH | like liquid chocolate | 9.0 |

EXAMPLE 5

Representative Growth Curves

Following the procedure of Example 3, whey permeate culture medium with and without glucose supplementation was compared with Difco Penassay broth and BBL nutrient broth for its ability to support the growth of a representative variety of clinically important microorganisms. The results are shown in Table 9.

TABLE 9

REPRESENTATIVE GROWTHS IN LIQUID MEDIA

| Microorganism | Whey Permeate Media | Whey Permeate Media w/ Glucose | DIFCO Penassay Broth | BBL Nutrient Broth |
|---|---|---|---|---|
| Bacillus subtilis 6051a | ++++ | not done | ++++ | ++++ |
| Escherichia coli HS | ++++ | not done | ++++ | ++++ |
| Enterobacter aerogenes E13048 | ++++ | not done | ++++ | ++++ |
| Streptococcus faecalis E19433 | ++++ | ++++ | ++++ | ++ |
| Staphylococcus aureus 6538P | ++++ | ++++ | ++++ | ++++ |
| Proteus mirabilis 25933 | ++++ | ++++ | ++++ | ++++ |
| Klebsiella pneumoniae 23357 | ++++ | ++++ | ++++ | ++++ |
| Pseudomonas fluorescens 15453 | ++++ | ++++ | ++++ | ++++ |
| Salmonella typhimurium LT2 | ++++ | ++++ | ++++ | ++++ |
| Shigella sonnei | ++++ | ++++ | ++++ | ++++ |
| Salmonella typhimurium 21a | +++ | ++++ | ++++ | +++ |

EXAMPLE 6

Effect of Autoclaving on Growth

In order to evaluate the importance of achieving a neutral pH in the final product through the autoclaving process, a filter sterilized medium control was prepared corresponding to the medium used in Example 5 but in which the final pH was adjusted to pH 7 by the addition of HCl rather than as a result of the autoclaving treatment. The results are shown in Table 10.

TABLE 10

REPRESENTATIVE GROWTHS IN LIQUID MEDIA

| Microorganism | Autoclaved Whey Permeate Media (supp) | Filtered Whey Permeate Media (supp) | DIFCO Penassay Broth | BBL Nutrient Broth |
|---|---|---|---|---|
| Bacillus subtilis 6051a | ++++ | ++++ | ++++ | ++++ |
| Escherichia coli HS | ++++ | ++++ | ++++ | ++++ |

TABLE 10-continued

REPRESENTATIVE GROWTHS IN LIQUID MEDIA

| Microorganism | Autoclaved Whey Permeate Media (supp) | Filtered Whey Permeate Media (supp) | DIFCO Penassay Broth | BBL Nutrient Broth |
|---|---|---|---|---|
| Enterobacter aerogenes E13048 | ++++ | ++++ | ++++ | ++++ |
| Streptococcus faecalis E19433 | ++++ | ++++ | ++++ | +++ |
| Staphylococcus aureus 6538P | +++ | +++ | +++ | +++ |
| Proteus mirabilis 25933 | ++++ | ++++ | ++++ | ++++ |
| Klebsiella pneumoniae 23357 | ++++ | ++++ | ++++ | ++++ |
| Pseudomonas fluorescens 15453 | ++++ | ++++ | ++++ | ++++ |
| Salmonella typhimurium LT2 | ++++ | ++++ | ++++ | ++++ |
| Shigella sonnei | ++++ | ++++ | ++++ | +++ |
| Salmonella typhimurium 21a | + | +++ | ++++ | − |

It can be seen from the last entry on the above table that there are apparently some nutrients required for the growth of *Salmonella typhimurium* which are changed by the autoclaving treatment and become not as readily metabolizable as in the sterile filtered medium.

EXAMPLE 7

Preparation of Anaerobic Medium

Using the previously indicated formula and following the procedure of L. V. Holdeman et al. (Ed.) in Anaerobe Laboratory Manual, 4th Edition (1977), a pre-reduced anaerobic culture medium was prepared by weighing out the dry ingredients immediately before use, adding water and resazurin, and heating under a nitrogen atmosphere. The solution was gently boiled until the resazurin turned from blue to pink to colorless in 5-10 minutes. After cooling in an ice bath under a nitrogen atmosphere, the cysteine was added. This was done after partial reduction of the medium by boiling in order to prevent oxidation of the cysteine, since oxidized crysteine can be toxic for some fastidious anaerobes. The pH was adjusted to 7.8 with NH$_4$OH as measured by test paper while bubbling nitrogen through the liquid, which was then dispensed into tubes which had been flushed with nitrogen. To prepare tubes of pre-reduced agar medium, agar was first added to the tubes to give the final concentration desired, and pre-reduced broth medium added to the agar in the tubes. After autoclaving at 15 psi for 20 minutes, the remaining solid agar was dissolved by inverting the tubes several times.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

Industrial Applicability

As can be seen from the present specification and examples, the present invention is industrially useful in providing a variety of commercially useful products from deproteinized whey permeate which has normally been considered a waste material.

What is claimed is:

1. A dry powder microbiological culture medium which can be reconstituted with water and autoclaved to form a clear, pH neutral culture medium capable of supporting the growth of microorganisms under suitable growth conditions, said culture medium being prepared by a process consisting essentially of:
   (a) raising the pH of a dairy whey lactose permeate having a pH below about 7 to a selected pH between pH 8 and pH 10 at which essentially all of the dissolved solids which would become insoluble when the permeate is autoclaved for 10-20 minutes at 121 degrees C. and 15 psi precipitate as microcrystalline solids;
   (b) separating the supernatant from the resulting precipitate to form a microcrystalline solid phase consisting essentially of said previously dissolved solids;
   (c) removing components having a molecular weight above about 100 kdal from the supernatant to form a lactose-rich supernatant which is essentially free of said dissolved solids; and
   (d) drying the resultant supernatant to form said dry powder microbiological culture medium.

2. A dry powder microbiological culture medium according to claim 1 wherein said components have been removed in step (c) by ultrafiltration across a filter which retains components having a molecular weight above about 100 kdal.

3. A dry powder microbiological culture medium according to claim 2 wherein said filter retains components having a molecular weight above about 20 kdal.

4. A dry powder microbiological culture medium according to claim 1 further containing an added source of nontoxic assimilable carbon atoms.

5. A dry powder microbiological culture medium according to claim 4 wherein said source is glucose.

6. A dry powder microbiological culture medium according to claim 1 further containing an added source of nontoxic assimilable nitrogen atoms.

7. A dry powder microbiological culture medium according to claim 6 wherein said source is a yeast extract, hydrolyzed casein, or mixtures thereof.

8. A dry powder microbiological culture medium according to claim 1 further containing an added gelling agent in an amount capable of forming a gel when said dry powder is admixed with water.

9. A dry powder microbiological culture medium according to claim 8 further containing hydrolyzed casein, yeast extract, cysteine HCl, and glucose added in amounts effective to produce a microbiological culture medium suitable for the cultivation of both aerobic and anaerobic bacteria.

10. A dry powder microbiological culture medium according to claim 1 further containing hydrolyzed casein, yeast extract, and glucose added in amounts effective to produce a general purpose microbiological growth medium.

11. A dry powder microbiological culture medium according to claim 1 further containing hydrolyzed casein, yeast extract, glucose, and a colorimetric oxidation-reduction indicator added in amounts effective to produce a culture medium suitable for the cultivation of anaerobic bacteria.

12. A sterile microbiological culture medium consisting essentially of an aqueous solution of the dry powder culture medium according to claim 1.

13. A sterile microbiological culture medium according to claim 12 which has been sterilized by autoclaving.

14. A sterile microbiological culture medium according to claim 12 having a solids content of about 3.5% (wt/vol).

15. A sterile microbiological culture medium according to claim 12 having a total glucose content of about 0.5% and further containing additives of about 0.5% hydrolyzed casein and about 0.05% yeast extract to produce a general purpose microbiological growth medium.

16. A sterile microbiological culture medium according to claim 12 having a total glucose content of about 0.4% and further containing additives of a nontoxic gelling agent in an amount effective to reduce oxygen diffusion, about 0.5% hydrolyzed casein, and about 0.05% yeast extract to produce a microbiological culture medium suitable for the cultivation of both aerobic and anaerobic bacteria.

17. A sterile microbiological culture medium according to claim 12 having a total glucose content of about 0.5% and further containing additives of about 0.5% hydrolyzed casein, about 1% yeast extract, about 0.2% cysteine HCl, about 0.5% hemin, about 0.1% vitamin $K_3$, and an effective amount of a colorimetric oxidation-reduction indicator and having a pH of about 7.8 and an oxidation-reduction potential of $-150$ mV or less to produce a culture medium suitable for the cultivation of anaerobic bacteria.

* * * * *

UNITED STATES PATENT AND TRADEMARK OFFICE
CERTIFICATE OF CORRECTION

PATENT NO. : 4,544,637

DATED : October 1, 1985

INVENTOR(S) : Kathleen M. Keggins et al.

It is certified that error appears in the above—identified patent and that said Letters Patent is hereby corrected as shown below:

Title page and column 1, line 2 and 3:

In the title of the invention, change "DIARY" to

--- DAIRY ---.

Signed and Sealed this

Third Day of December 1985

[SEAL]

Attest:

Attesting Officer

DONALD J. QUIGG

Commissioner of Patents and Trademarks